US008932980B2

(12) United States Patent
Darbha et al.

(10) Patent No.: US 8,932,980 B2
(45) Date of Patent: Jan. 13, 2015

(54) ORDERED MESOPOROUS TITANOSILICATE AND THE PROCESS FOR THE PREPARATION THEREOF

(75) Inventors: Srinivas Darbha, Pune (IN); Anuj Kumar, Pune (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days.

(21) Appl. No.: 13/811,235

(22) PCT Filed: Jul. 20, 2011

(86) PCT No.: PCT/IN2011/000478
§ 371 (c)(1),
(2), (4) Date: Jan. 18, 2013

(87) PCT Pub. No.: WO2012/011124
PCT Pub. Date: Jan. 26, 2012

(65) Prior Publication Data
US 2013/0116453 A1    May 9, 2013

(30) Foreign Application Priority Data

Jul. 20, 2010  (IN) .......................... 1696/DEL/2010

(51) Int. Cl.
| | | |
|---|---|---|
| B01J 31/06 | (2006.01) |
| C07D 301/03 | (2006.01) |
| C07C 259/00 | (2006.01) |
| C07C 217/00 | (2006.01) |
| C07C 211/00 | (2006.01) |
| C07C 37/00 | (2006.01) |
| B01J 21/06 | (2006.01) |
| B01J 29/89 | (2006.01) |
| C01B 37/00 | (2006.01) |
| C07C 37/60 | (2006.01) |
| C07C 213/04 | (2006.01) |
| C07C 249/04 | (2006.01) |
| C07D 301/14 | (2006.01) |
| C07C 215/68 | (2006.01) |
| C07C 215/70 | (2006.01) |
| C07D 301/19 | (2006.01) |

(52) U.S. Cl.
CPC ................ B01J 21/063 (2013.01); B01J 29/89 (2013.01); C01B 37/005 (2013.01); C07C 37/60 (2013.01); C07C 213/04 (2013.01); C07C 249/04 (2013.01); C07D 301/14 (2013.01); C07C 215/68 (2013.01); C07C 215/70 (2013.01); C07D 301/19 (2013.01); C07B 2200/09 (2013.01); C07C 2101/14 (2013.01)
USPC ........... 502/242; 549/523; 564/267; 564/355; 564/431; 568/741

(58) Field of Classification Search
USPC ........... 549/523; 564/267, 355, 431; 568/741; 502/242
See application file for complete search history.

(56) References Cited

PUBLICATIONS

Guidotti et al, Epoxidation of unsaturated FAMEs obtained from vegetable source over Ti(IV)-grafted silica catalyst : A comparison between ordered and non-ordered mesoporous materials, 2006, Journal of Molecular Catalysis A : Chemical, 250, p. 218-225.*
Shah et al, Direct synthesis of Ti-containing SBA-16-type mesoporous material by the evaporation-induced self-assembly method and its catalytic performance for oxidative desulfurization, Journal of Colloid and Interface Science, 2009, 336, p. 707-711.*
Park et al, the Study of the Oxidative Desulfurization of 4,6-DMDBT over Ti-SBA-16 catalyst, 2009, Korea Research Institute Chemical Technology, a summary sheet.*

* cited by examiner

*Primary Examiner* — T. Victor Oh
(74) *Attorney, Agent, or Firm* — Ladas & Parry LLP

(57) ABSTRACT

The invention discloses three-dimensional, ordered, mesoporous titanosilicates wherein the Ti is in a tetrahedral geometry and exclusively substituted for Si in the silica framework. Such titanosilicates find use as catalysts for epoxidation, hydroxylation, C—H bond oxidation, oxidation of sulfides, aminolysis of epoxide and amoximation, with approx. 100% selectivity towards the products.

9 Claims, 7 Drawing Sheets

ORDERED MESOPOROUS TITANOSILICATE AND THE PROCESS FOR THE PREPARATION THEREOF

RELATED APPLICATION INFORMATION

This application is a 371 of International Application PCT/IN2011/000478 filed 20 Jul. 2011 entitled "ORDERED MESOPOROUS TITANOSILICATE AND THE PROCESS FOR THE PREPARATION" which was published in the English language on 26 Jan. 2012, with International Publication Number WO2012/011124 A1, and which claims priority from Indian Patent Application No.: 1696/DEL/2010 filed 20 Jul. 2010, the contents of which are incorporated herein by reference.

FIELD OF THE INVENTION

The present invention relates to ordered mesoporous titanosilicates and a process to prepare thereof. The invention further discloses the use of such titanosilicates for selective catalytic oxidations and aminolysis of epoxides.

BACKGROUND OF THE INVENTION

Titanosilicates are class of solid oxidation catalysts. Crystalline, microporous titanium silicalites (TS-1 and TS-2; U.S. Pat. Nos. 4,410,501 and 1,001,038 and Reddy et al., Appl. Catal. Vol. 58, page L1, year 1990) exhibit highly efficient catalytic activity for oxidation of organic molecules. However, their applicability is limited to only organic molecules with less than 0.5 nm diameter. Mesoporous titanosilicates should overcome this limitation in applicability. However, Ti substituted in mesoporous M41S family silica materials discovered in subsequent years (Corma et al., J. Chem. Soc. Chem. Commun. Page 147, year 1994; Tanev et al., Nature, vol. 368, page 321, year 1994) are thermally less stable (structure collapses at 873 K and in presence of water). While issues related to pore size limitation have been over come with these materials, they exhibit oxidation activity/selectivity lower than those of microporous TS-1 and TS-2. Their thinner pore walls are the cause for their low thermal stability. Unlike in TS-1, Ti in M41S material is located mostly on the pore walls and not substituted in silica framework locations. This is one of the main reasons for their low catalytic activity/selectivity. Moreover, Ti-MCM-41 is only a two-dimensional pore material. Ti—SBA-15 has thicker wall but it is also having a two-dimensional pore architecture (Morey et al., Chem. Mater. Vol. 12, page 898, year 2000). Most of the titanosilicates reported so far have been prepared by post-synthesis methods wherein a structured silica matrix is prepared first and then, titanium is loaded by grafting techniques on the silica structure. In all those materials Ti is located on the pore walls as extra framework nano titanium oxide phase. Such nano-oxide phases are less reactive in selective oxidation reactions. Materials prepared by the in-situ and direct synthesis method can lead to Ti substituted in the framework of silica possessing a tetrahedral geometry. Several mesoporous titanosilicates with different structural and pore architectures have been reported and prepared by direct synthesis methods in basic conditions. They all have thinner pore wall and are thermally less stable (<873 K). Preparation in acidic conditions leads to materials with unique structures and properties. Ti incorporation in those materials is a challenging task. Several micro-mesoporous and amorphous materials have been known but all them have the above disadvantages. A material with, ordered, three-dimensional pore structure and Ti in framework locations would enhance the reaction rate by facilitating diffuse of reactant and product molecules through the interconnected, ordered, 3-dimensional pores which is otherwise not possible with 2-dimensional titanosilicate structures. Because of the facile diffusion of reactant and product molecules in 3-dimensional mesopore structures, pore plugging/blocking which is normally anticipated and observed leading to deactivation of microporous titanosilicate materials can be avoided. In view of all these advantageous features and their applicability in transformation of bulky molecules of pharmaceutical interest, a stable, ordered mesoporous, titanosilicate with three-dimensional pore structure and Ti located in the framework tetrahedral Si location is more efficient and hence, desirable for oxidation and acid catalyzed aminolysis of epoxides reactions. Often in the synthesis of titanosilicates, instead of titanium getting substituted in the framework it gets precipitated as a separate nano phase on the mesoporous surfaces. Preparation of three dimensional mesoprous materials with thick pore walls and titanium being isolated and substituted in the framework tetrahedral location is a challenging task.

Anuj Kumar et al (Chem. Commun. pages 6484-6486, year 2009) reported the preparation of Ti—SBA-12 and its application in oxidation reactions. This material belongs to the class of hexagonal pore arrangement. While Ti possesses tetrahedral structure, it has a tripodal $Ti(OSi)_3OH$ geometry as revealed by EPR and UV-visible spectroscopy and selectivity for epoxide in cyclohexene conversion is not 100%. Also the conversion of cyclooctene a bulkier molecule is only 61%. This material has low wall thickness. Shen et al (J. Mater. Sci., vol. 42, pp. 7057-7061, year 2007) reported Ti—SBA-16 but Ti in this material has octahedral geometry (UV band 330 nm; Raman band 144 $cm^{-1}$) and present mostly as an extra framework anatase-like titania phase. Ti is not substituted in the framework and hence, will not be active in oxidation reactions. Further oxidation reactions catalyzed by this Ti—SBA-16 will lead to non-selective oxidations and decomposition of oxidants. Also, this material has lower surface area and pore diameter leading to lower activity. Carlos et al (Catal. Today Vol. 107-108, pp. 578-588, year 2005) reported preparation of Ti—SBA-16 by post synthesis method. Again Ti is present as a extra-lattice anatase phase. Ti is located on the surface of pores but not in the framework as an active form for oxidation reactions. Shah et al in "Direct synthesis of Ti-containing SBA-16-type mesoporous material by the evaporation-induced self-assembly method and its catalytic performance for oxidative desulfurization" published in Journal of Colloid and Interface Science; Volume 336, Issue 2, 15 Aug. 2009, Pages 707-711 describes novel Ti-containing SBA-16-type mesoporous material (with various Ti loadings of 5, 10, and 15 wt %), synthesized by an evaporation-induced self-assembly method using F127 copolymer as template. But this material leads to a different disordered material affecting diffusion and reaction rates adversely.

An article titled "*Direct Synthesis of Titanium Incorporated SBA-16 Molecular Sieves*" by Govindasamy Chandrasekar et. al; published in Theories and Applications of Chem. Eng., 2008, Vol. 14, No. 1 describes highly ordered three dimensional (3-D) cubic TiSBA-16 molecular sieves with different $n_{Si}/n_{Ti}$ ratio prepared through direct synthesis under highly acidic condition. The structure and the textural properties of the materials were characterized by X-ray diffraction, $N_2$ physisorption, SEM, and TEM analysis. The nature and the coordination of the Ti atoms in SBA-16 prepared with various Ti content were investigated by UV-vis spectroscopy. Further, states that the Ti atoms are well-dispersed and mostly occupy the tetrahedral coordination.

OBJECTIVES OF THE INVENTION

The main objective of the present invention is to provide a titanosilicate having a three-dimensional, cubic, interconnected, cage-like pore structure with Ti in a tetrahedral geometry and substituted for Si in the silica framework, the said titanosilicate is thermally stable even at temperatures as high as 1073 K.

One more object of the present invention is to provide a process for preparing ordered mesoporous titanosilicates for selective catalytic oxidations and aminolysis of epoxides.

Another object is to provide a process for preparing highly efficient, mesoporous titanosilicate catalyst for selective oxidation of bulkier organic molecules wherein the catalyst catalyzes a range of oxidation reactions at ambient conditions with near complete conversion and selectivity close to 100%.

Yet another object of the present invention is to provide an efficient process for preparation of titanosilicate at 298-313 K.

Yet another object of the present invention is to provide a process for oxidation of organics such as hydrocarbons with $H_2O_2$ or organic hydroperoxides at mild conditions over the catalysts of the present invention. The oxidation reactions which the catalyst can catalyze include epoxidation, hydroxylation of aromatics, C—H bond oxidation, oxidation of alcohols, oxidation of sulfides, amoximation and related such reactions.

Still yet another object of the present invention is to provide a process for the oxidation of bulkier molecules like cyclohexene, cyclooctene, cyclodecene and naphthalene.

While one or more of the above characteristic features may be present in the prior art titanosilicates, the presence of all the features is hitherto unknown. While the prior-art titanosilicates may possess mesoporous and tetrahedral structure they do not possess three-dimensional cubic pore arrangement similar to SBA-16 structure, Im(-3)m space group and titanium substituted exclusively in the framework with $Ti(OSi)_4$ geometry.

SUMMARY OF THE INVENTION

Accordingly, the present invention provides ordered mesoporous titanosilicate (Ti—SBA-16), wherein said three-dimensional mesoporous titanosilicate having a composition represented by the general formula $$Ti_xSi_{1-x}O_2$$

wherein x ranges from 0.001-0.05, with Ti is in a tetrahedral geometry and exclusively substituted for Si in the silica framework.

In one embodiment of the invention, said titanosilicate comprises three-dimensional, cubic, interconnected, cage-like pore structure.

In another embodiment of the invention, Si/Ti molar ratio ranges from 20-120.

In another embodiment of the invention, the invention relates to a process for the preparation of titanosilicate, wherein said process comprising the steps of:

a. reacting F127 tri-block co-polymer ($EO_{106}$—$PO_{70}$-$EO_{106}$; average mol. wt. 12,600) dissolved in water and conc. HCl with tetraethyl orthosilicate and Ti precursor dissolved in isopropanol at 298-313 K for a period ranging about 2 hours.

b. stirring the reaction mixture as obtained in step (a) for 20-24 hours to form a gel;

c. crystallising the gel as obtained in step (b) at 353-373 K for 40-50 h to obtain titanosilicate (Ti—SBA-16);

d. washing titanosilicate as obtained in step (c) with water and drying at 373-423 K followed by calcining in air at 823 K for 6-12 h to obtain titanosilicate (Ti—SBA-16).

In another embodiment of the invention, said Ti precursor used in step (a) is selected from Ti compounds, preferably Ti-isopropoxide.

In another embodiment of the invention, mole ratio of the F127 triblock copolymer ranges between 0.55-0.6 moles.

In another embodiment of the invention, invention relates to an improved process for oxidation of aromatics using titanosilicate catalyst, wherein the said process comprises the steps of:

a. charging a titanosilicate catalyst, aromatic reactant and an oxidant in molar ratio preferably in the range of 0.5-2 with respect to aromatic reactant, a solvent and optionally ammonia in a flask;

b. heating the reaction mixture as obtained in step (a) at 313-353 K for 6 to 24 hrs to obtain desired product.

In another embodiment of the invention, aromatic reactant used in step (a) is selected from the group consisting of of cyclohexene, cyclooctene, cyclohexanone and naphthalene.

In another embodiment of the invention, solvent used in step (a) is selected from the group of dichloromethane, chloroform, dichloroethane, acetone, water and acetonitrile.

In another embodiment of the invention, the oxidant used in step (a) is selected from the group of non-aq. TBHP(tert. Butyl hydroperoxide), $H_2O_2$, cumene hydroperoxide and 70% aq TBHP.

In another embodiment of the invention, said titanosilicate is used as catalyst in the range of 3-13% with respect to aromatic reactant.

In another embodiment of the invention, said titanosilicate is reusable.

In another embodiment of the invention, conversion of the aromatic reactant ranges between 80 to 92.7% and selectivity of product ranges between 93-100%.

In another embodiment of the invention, the invention relates to use of ordered mesoporous titanosilicate prepared by the process of present invention for epoxidation, hydroxylation, C—H bond oxidation, oxidation of sulfides, aminolysis of epoxides and amoximation.

DETAILED DESCRIPTION OF THE INVENTION

Figure 1:
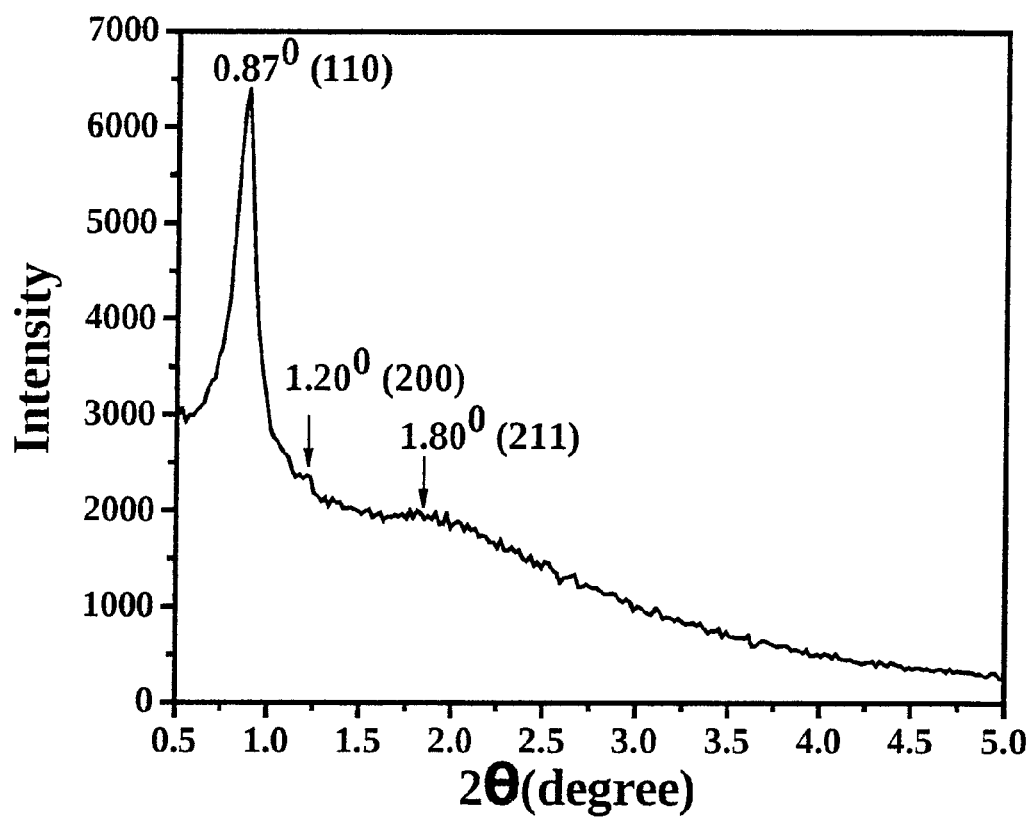
FIG. 1 depicts the XRD pattern of titanosilicate sample with Si/Ti=30
Figure 2:
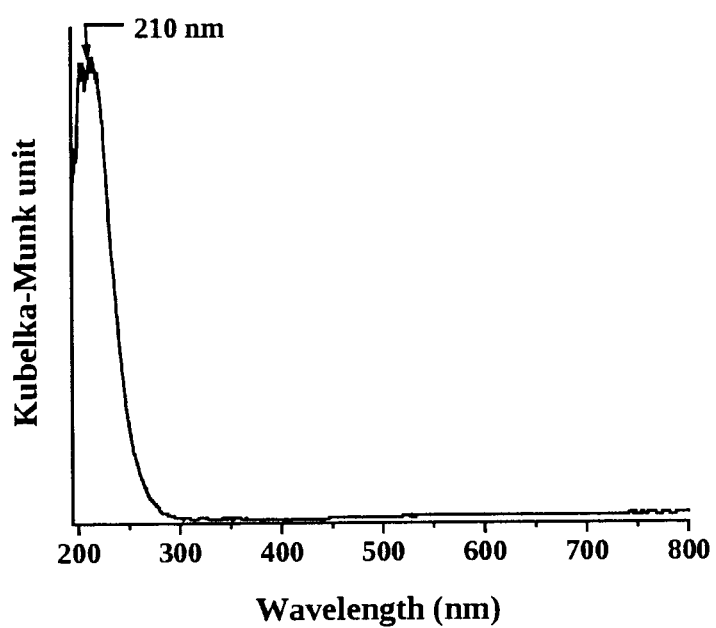
FIG. 2 Diffuse reflectance UV-Visible spectrum of titanosilicate sample (Si/Ti molar ratio=30) showing the characteristic charge transfer band arising from framework substituted tetrahedral titanium.
Figure 3:
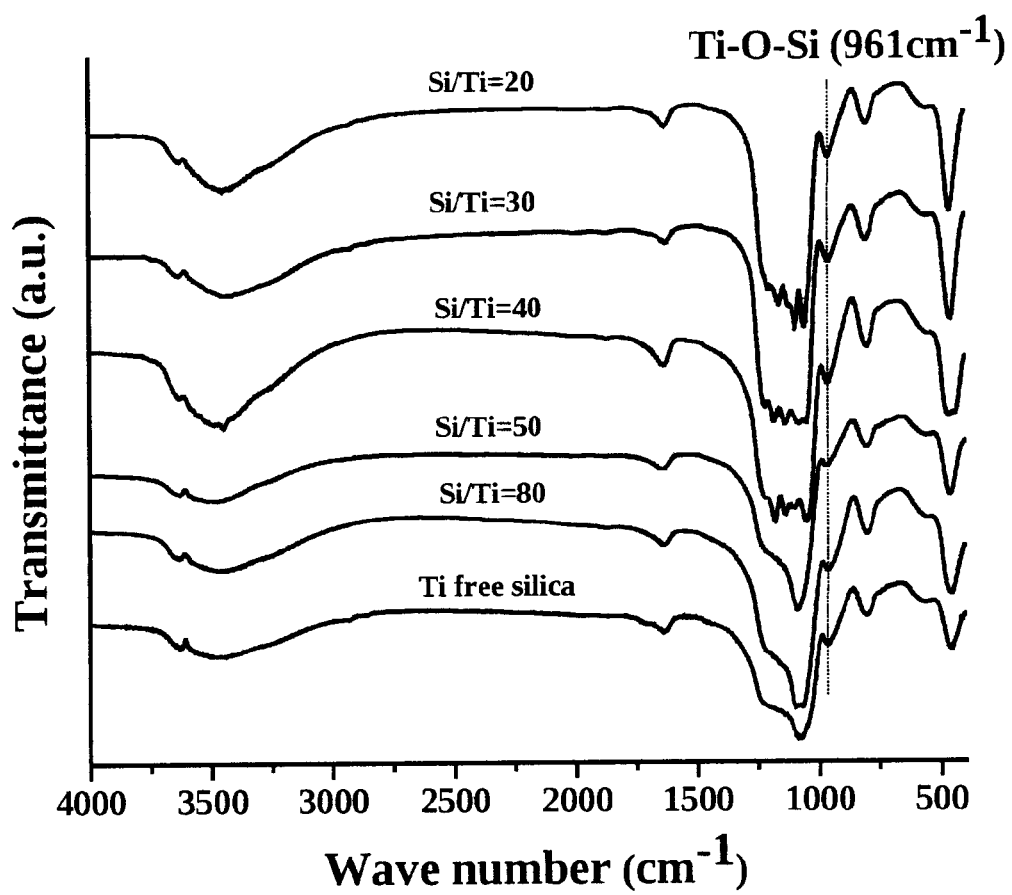
FIG. 3 FT-IR spectra of titanosilicate samples with different Si/Ti ratio showing a characteristic band at 961 cm$^{-1}$ due to Ti—O—Si vibrations FIG. 4 FT-Raman spectrum of mesoporous titanosilicate sample (Si/Ti=30) showing the characteristic band at 967 cm$^{-1}$ due to framework substituted Ti—O—Si.
Figure 4:
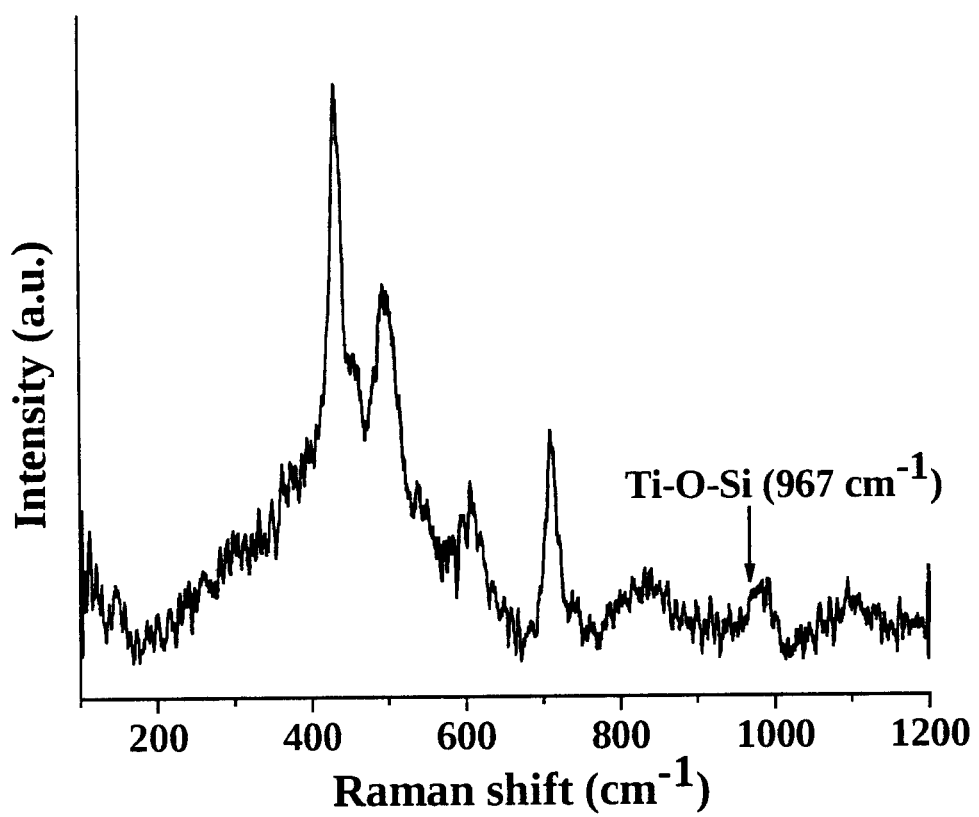
Figure 5:
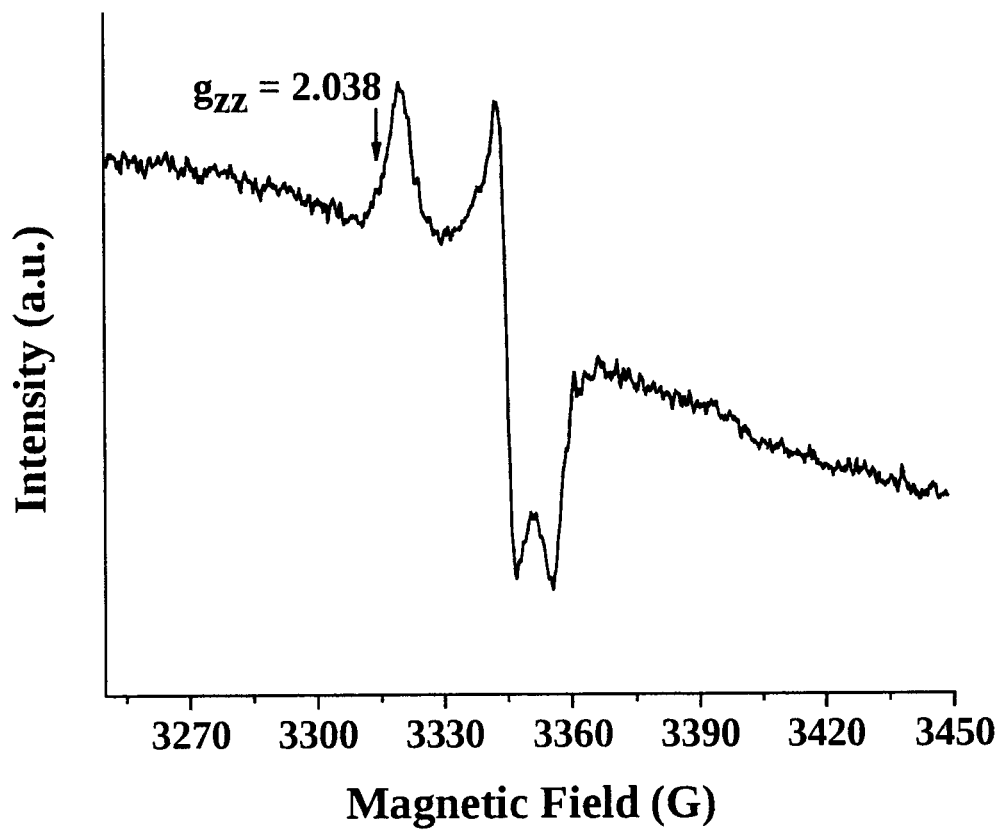
FIG. 5 EPR spectrum of superoxo-Ti generated on mesoporous titanosilicates of present invention (Si/Ti molar ratio=30). Arrow marks the signal arising from tetrahedral—tetrapodal Ti species.
Figure 6:
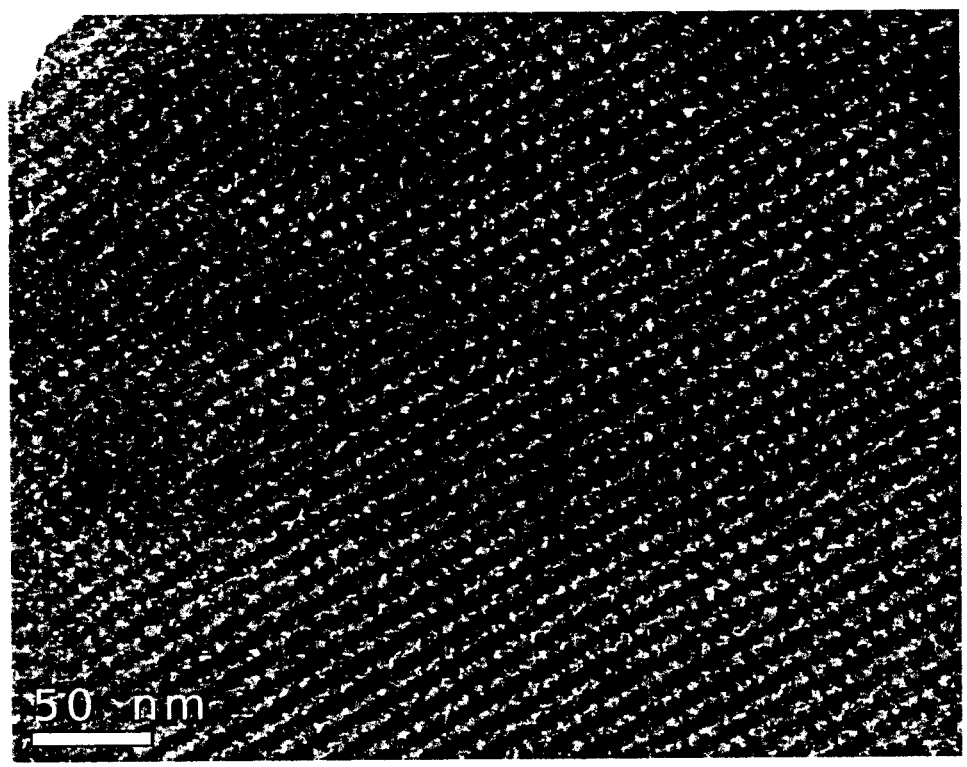
FIG. 6 High resolution transmission electron micrograph of titanosilicate (Si/Ti=20) showing long-range 3-dimensional, mesoporous ordering and inter-connected cage-like structure.
Figure 7:
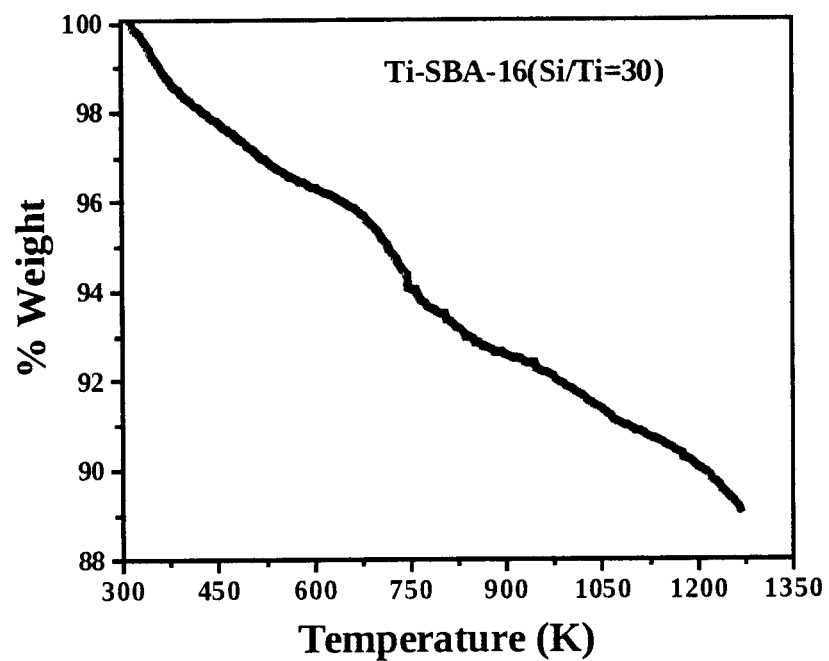
FIG. 7 Thermogravimetric analysis of a representative titanosilicate sample with Si/Ti=30. The weight loss observed is due to condensation of silanol groups only.

The present invention provides ordered mesoporous titanosilicates, a process for preparing said titanosilicates and using them for selective catalytic oxidations. The titanosilicate of the invention has a molar composition in terms of anhydrous oxides of $TiO_2$ and $SiO_2$, wherein the ratio of Si/Ti ranges from 20-120, a three-dimensional, cubic, interconnected, cage-like pore structure and with Ti in a tetrahedral geometry and exclusively substituted for Si in the silica framework.

In a preferred embodiment of the titanosilicate of the invention, said three-dimensional mesoporous titanosilicate has the physicochemical characteristics listed in Table 1.

TABLE 1

Physicochemical characteristics of mesoporous titanosilicate

| Structure: | |
|---|---|
| Crystal system | Cubic |
| Space group | Im(-3)m |
| Pore dimensionality | Three-dimensional |
| Unit cell parameter (a in nm) | 14.3-15.3 |
| XRD peaks for (110), (200) and (211) | 0.79-0.87°, 1.14-1.22° and 1.74-1.89°, respectively |
| Designated structural name | Ti-SBA-16 |
| Morphology: | Spherical & plate-like |
| Elemental composition: | |
| Si/Ti (molar ratio) | 120-20 |
| Textural Characteristics: | |
| Total surface area ($S_{BET}$, m$^2$/g) | 750-1000 |
| Average pore diameter (nm) | 3.3-4 |
| Total pore volume (cc/g) | 0.6-0.9 |
| Thickness of the pore wall (nm) | 8.6-9.6 |
| Spectral characteristics: | |
| FT-IR band due to Si—O—Ti (in cm$^{-1}$) | 960-965 |
| Raman band due to Si—O—Ti (in cm$^{-1}$) | 963-968 |
| Diffuse reflectance UV-visible band (in nm) | 210-212 |
| EPR signal ($g_{zz}$ value for superoxo speices) | 2.038-2.020 |
| Thermal analysis: | |
| % Weight loss (between 298 and 1300K) | 7.5-11 |
| Thermal stability | ≥1073K |

The titanosilicate of the invention is characterized by
(a) Im(-3)m crystal space group with cubic unit cell parameter (a) in the range 14.3-15.3 nm,
(b) low-angle X-ray diffraction peaks at 0.79-0.87°, 1.14-1.22° and 1.74-1.89° indexable to (110), (200) and (211) planes,
(c) pore wall thickness in the range 8.6-9.6 nm,
(d) the absorption band at 208-212 nm in the UV spectrum corresponding to tetrahedral $Ti(OSi)_4$ geometry
(e) the absorption band at 960-965 cm$^{-1}$ in the Raman and IR spectra corresponding to Si—O—Ti linkages, and
(f) EPR ($g_{zz}$) signal at 2.038-2.028 for superoxo species generated upon contact with $H_2O_2$ and said catalyst catalyzes a range of oxidation reactions at ambient conditions with near complete conversion and selectivity close to 100%.

In an embodiment of the invention, the titanosilicates are used in the oxidation reactions in powder form or in formulated and shaped form preferably as extrudes or spheres.

In one embodiment of the invention, the titanosilicate has a thick pore wall making it thermally more stable.

In yet another embodiment of the invention, the titanosilicate has thermal stability greater than or equal to 1073 K.

The present invention provides a process for preparation of mesoporous titanosilicate of the invention, wherein said titanosilicate catalyst of present invention is prepared by a process comprising:
a. reacting F127 tri-block co-polymer ($EO_{106}$—$PO_{70}$-$EO_{106}$; average mol. wt. 12,600) dissolved in distilled water and HCl with tetraethyl orthosilicate and Ti precursor dissolved in isopropanol at 298-313 K;
b. stirring the mixture of step (a) for 20-24 hours to form a gel;
c. crystallising the gel of step (b) at 353-373 K for 40-50 h to obtain titanosilicate (Ti—SBA-16);
d. washing with water and drying at 373-423 K and calcining in air at 823 K for 6-12 h to obtain titanosilicate (Ti—SBA-16).

The present invention also provides a process for oxidation of organics such as hydrocarbons with $H_2O_2$ or organic hydroperoxides at mild conditions over the catalysts of the present invention. The oxidation reactions that the catalyst can catalyze include epoxidation, hydroxylation of aromatics, C—H bond oxidation, oxidation of alcohols, oxidation of sulfides, amoximation and related such reactions.

The titanosilicate of the present invention is efficient for the oxidation of bulkier molecules. The oxidation of organics is carried out with oxidants such as $H_2O_2$ and organic hydroperoxides such as tert. butyl hydroperoxide and cumene hydroperoxide.

In another embodiment, the titanosilicate is active for oxidation of cyclohexene, cyclooctene, cyclodecene, naphthalene, anthracene, styrene, stilbene, pinene, phenol, naphthol and such like molecules.

In another embodiment, the titanosilicate is effective for oxidation of bulkier organic molecules of pharmaceutical interest.

In yet another embodiment of the invention, the titanosilicate is highly active for epoxidation, hydroxylation, C—H bond oxidation, oxidation of sulfides, amoximation and like such oxidation reactions.

In another embodiment of the present invention, the titanosilicate is highly active for oxidation of bulkier hydrocarbons.

In another embodiment of the present invention, the titanosilicate is highly active for aminolysis of epoxides.

In another embodiment of the present invention, the oxidant to substrate molar ratio in the oxidation reaction is preferably in the range of 0.5-2, wherein the substrate refers to compound which is to be oxidized.

In yet another embodiment of the present invention, the amount of catalyst used in the oxidation reaction, lies preferably in the range 3-13 wt % of the substrate.

In still yet another embodiment the solid catalyst is stable and reusable.

In still another embodiment the concentration of F127 co-polymer used in catalyst synthesis is preferably in the range 0.55-0.60 moles.

It is a feature of the process of present invention that the catalyst is a solid and the reaction takes place in a heterogeneous condition, and the solid catalyst can be easily separated from products by centrifugation/filtration for further reuse.

Another feature of the process of present invention that the oxidation reactions are conducted at moderate conditions and preferably at 40-100° C. and 1 bar pressure.

In yet another feature, the per-pass conversion in the oxidation reaction is in the range 80-100% and selectivity 95-100%.

The process of the present invention is highly eco-friendly and economical and has overcome issues related to pore plugging with reactants and product molecules, unlike those of the prior art titanosilicate catalysts, due to their mesoporosity and three-dimensional pore structure. The processes involving the present invention catalysts are more sustainable and generate little waste as conversions and selectivities for desired products in oxidation reactions are nearly 100%.

The present invention is illustrated herein below with examples, which are illustrative only and should not be construed to limit the scope of the present invention in any manner.

EXAMPLE 1

This example illustrates the preparation of mesoporous titanosilicate (Ti—SBA-16) of the present invention with Si/Ti molar ratio of 80. 7.391 g of F127 tri-block co-polymer ($EO_{106}$—$PO_{70}$-$EO_{106}$; average mol. wt. 12,600) was dissolved in 315.6 g of distilled water and 68.7 g of conc. HCl at 313 K with stirring for 2 h. To it, 28.34 g of tetraethyl orthosilicate (98%) was added over 30 min. 0.48 g of Ti-isopropoxide (98%) dissolved in 10 ml of isopropanol was, then, added. Stirring was continued for 20 h. The gel formed was transferred to a Teflon-lined stainless steel autoclave. It was crystallized at 353 K for 48 h. The solid formed was recovered, washed with water, dried at 373 K for 12 h and calcined in air at 823 K for 8 h.

EXAMPLE 2

This example illustrates the preparation of mesoporous titanosilicate (Ti—SBA-16) of the present invention with Si/Ti molar ratio of 50. 7.391 g of F127 tri-block co-polymer ($EO_{106}$—$PO_{70}$-$EO_{106}$; average mol. wt. 12,600) was dissolved in 315.6 g of distilled water and 68.7 g of conc. HCl at 313 K with stirring for 2 h. To it, 28.34 g of tetraethyl orthosilicate (98%) was added over 30 min. 0.773 g of Ti-isopropoxide (98%) dissolved in 10 ml of isopropanol was, then, added. Stirring was continued for 20 h. The gel formed was transferred to a Teflon-lined stainless steel autoclave. It was crystallized at 353 K for 48 h. The solid formed was recovered, washed with water, dried at 373 K for 12 h and calcined in air at 823 K for 8 h.

EXAMPLE 3

This example illustrates the preparation of mesoporous titanosilicate (Ti—SBA-16) of the present invention with Si/Ti molar ratio of 40. 7.391 g of F127 tri-block co-polymer ($EO_{106}$—$PO_{70}$-$EO_{106}$; average mol. wt. 12,600) was dissolved in 315.6 g of distilled water and 68.7 g of conc. HCl at 313 K with stirring for 2 h. To it, 28.34 g of tetraethyl orthosilicate (98%) was added over 30 min. 0.966 g of Ti-isopropoxide (98%) dissolved in 10 ml of isopropanol was, then, added. Stirring was continued for 20 h. The gel formed was transferred to a Teflon-lined stainless steel autoclave. It was crystallized at 353 K for 48 h. The solid formed was recovered, washed with water, dried at 373 K for 12 h and calcined in air at 823 K for 8 h.

EXAMPLE 4

This example illustrates the preparation of mesoporous titanosilicate (Ti—SBA-16) of the present invention with Si/Ti molar ratio of 30. 7.391 g of F127 tri-block co-polymer ($EO_{106}$—$PO_{70}$-$EO_{106}$; average mol. wt. 12,600) was dissolved in 315.6 g of distilled water and 68.7 g of conc. HCl at 313 K with stirring for 2 h. To it, 28.34 g of tetraethyl orthosilicate (98%) was added over 30 min. 1.288 g of Ti-isopropoxide (98%) dissolved in 10 ml of isopropanol was, then, added. Stirring was continued for 20 h. The gel formed was transferred to a Teflon-lined stainless steel autoclave. It was crystallized at 353 K for 48 h. The solid formed was recovered, washed with water, dried at 373 K for 12 h and calcined in air at 823 K for 8 h.

EXAMPLE 5

This example illustrates the preparation of mesoporous titanosilicate (Ti—SBA-16) of the present invention with Si/Ti molar ratio of 20. 7.391 g of F127 tri-block co-polymer ($EO_{106}$—$PO_{70}$-$EO_{106}$; average mol. wt. 12,600) was dissolved in 315.6 g of distilled water and 68.7 g of conc. HCl at 313 K with stirring for 2 h. To it, 28.34 g of tetraethyl orthosilicate (98%) was added over 30 min. 1.932 g of Ti-isopropoxide (98%) dissolved in 10 ml of isopropanol was, then, added. Stirring was continued for 20 h. The gel formed was transferred to a Teflon-lined stainless steel autoclave. It was crystallized at 353 K for 48 h. The solid formed was recovered, washed with water, dried at 373 K for 12 h and calcined in air at 823 K for 8 h.

The structural and textural properties of mesoporous titanosilicate prepared in examples 1-5 are listed in Table 2.

TABLE 2

Structural and textural properties of titanosilicates

| Example No. | Si/Ti | Unit cell parameter (a; nm) | Unit cell volume ($nm^3$) | $S_{BET}$ ($m^2$/g) | Pore diameter (nm) | Pore volume (cc/g) | Wall thickness (nm) |
|---|---|---|---|---|---|---|---|
| 1 | 80 | 14.68 | 3163.6 | 795 | 3.43 | 0.79 | 9.28 |
| 2 | 50 | 14.35 | 2955.0 | 909 | 3.82 | 0.86 | 8.60 |
| 3 | 40 | 15.22 | 2525.7 | 709 | 3.97 | 0.70 | 9.21 |
| 4 | 30 | 14.35 | 2955 | 765 | 3.50 | 0.67 | 8.92 |
| 5 | 20 | 15.04 | 3402.1 | 780 | 3.43 | 0.66 | 9.59 |

EXAMPLE 6

This example illustrates the epoxidation of cyclohexene with 70% aq. tert-butyl hydroperoxide (TBHP) in dichloromethane medium over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.45 g of 70% aq, TBHP and 5 ml of dichloromethane were taken in the round-bottomed flask. The reaction was conducted at 313 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=92.1%, cyclohexene epoxide selectivity=100%.

EXAMPLE 7

This example illustrates the epoxidation of cyclohexene with 70% aq. tert-butyl hydroperoxide (TBHP) in dichloroethane over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.45 g of 70% aq, TBHP and 5 ml of dichloroethane were taken in the round-bottomed flask. The reaction was conducted at 333 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=85.0%, cyclohexene epoxide selectivity=100%.

EXAMPLE 8

This example illustrates the epoxidation of cyclohexene with 70% aq. tert-butyl hydroperoxide (TBHP) in chloroform over Ti—SBA-16=30; example 4) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.45 g of 70% aq, TBHP and 5 ml of chloroform were taken in the round-bottomed flask. The reaction was conducted at 333 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=90.0%, cyclohexene epoxide selectivity=100%.

EXAMPLE 9

This example illustrates the epoxidation of cyclohexene with 5.5 M. tert-butyl hydroperoxide (TBHP) in decane over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.90 g of non-aq. TBHP and 5 ml of dichloromethane were taken in the round-bottomed flask. The reaction was conducted at 313 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=92.7%, cyclohexene epoxide selectivity=100%.

EXAMPLE 10

This example illustrates the epoxidation of cyclohexene with 5.5 M. tert-butyl hydroperoxide (TBHP) in decane over Ti—SBA-16 (Si/Ti=80; example 1) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.90 g of non-aq. TBHP and 5 ml of dichloromethane were taken in the round-bottomed flask. The reaction was conducted at 313 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=48.9%, cyclohexene epoxide selectivity=100%.

EXAMPLE 11

This example illustrates the epoxidation of cyclohexene with 5.5 M. tert-butyl hydroperoxide (TBHP) in decane over Ti—SBA-16 (Si/Ti=50; example 2) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.90 g of non-aq. TBHP and 5 ml of dichloromethane were taken in the round-bottomed flask. The reaction was conducted at 313 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion=56%, cyclohexene epoxide selectivity=100%.

EXAMPLE 12

This example illustrates the epoxidation of cyclohexene in dichloroethane with 5.5 M. tert-butyl hydroperoxide (TBHP) in decane over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 0.82 g of cyclohexene and 0.90 g of non-aq. TBHP and 5 ml of dichloroethane were taken in the round-bottomed flask. The reaction was conducted at 333 K for 12 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclohexene conversion =90.0%, cyclohexene epoxide selectivity =100%.

EXAMPLE 13

This example illustrates the epoxidation of cyclooctene in dichloroethane with 5.5 M. tert-butyl hydroperoxide (TBHP) in decane over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 1.15 g of cyclooctene (98%, Aldrich) and 0.90 g of non-aq. TBHP and 10 ml of dichloromethane were taken in the round-bottomed flask. The reaction was conducted at 313 K for 24 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclooctene conversion=92.1%, cyclooctene epoxide selectivity=100%.

EXAMPLE 14

This example illustrates the epoxidation of cyclooctene in acetone medium with 5.5 M. tert-butyl hydroperoxide (TBHP) in decane over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 1.15 g of cyclooctene (98%, Aldrich) and 0.90 g of non-aq. TBHP and 10 ml of acetone were taken in the round-bottomed flask. The reaction was conducted at 333 K for 24 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Cyclooctene conversion =79.6%, cyclooctene epoxide selectivity=100%.

EXAMPLE 15

This example illustrates the hydroxylation of naphthalene with aq. $H_2O_2$ in acetonitrile medium over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 1 g of naphthalene and 0.6 g of 30% aq, $H_2O_2$ and 10 ml of acetonitrile, were taken in the round-bottomed flask. The reaction was conducted at 353 K for 24 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Naphthalene conversion=50%, selectivity for 1-napthol and 2-naphthol are 90 and 10%, respectively.

EXAMPLE 16

This example illustrates the ammoximation of cyclohexanone over Ti—SBA-16 (Si/Ti=30; example 4) catalyst. The reactions were conducted in a glass, double-necked, round-bottomed flask fitted with a water-cooled condenser and a rubber septum to inject the oxidant. 0.1 g of the catalyst, 0.98 g of cyclohexanone and 1.14 g of 30% aq, $H_2O_2$, 1.02 g of 25% aq. ammonia solution and 5 ml of water, were taken in the round-bottomed flask. The reaction was conducted at 353 K for 6 h. The products were analyzed by gas chromatography (Varian 3400; CP-SIL8CB column; with a 30 m-long, and 0.53 mm-i.d.) and identified by GC-MS (Shimadzu QP-5000; with a 30 m-long, 0.25 mm-i.d., and 0.25 μm-thick capillary column DB-1). Conversion of cyclohexanone=98% and selectivity of oxime=94%.

EXAMPLE 17

This example illustrates reusability of the catalyst used in example 9. At the end of the reaction the catalyst was separated by centrifugation/filtration, washed with decane and then with acetone. Dried at 373 K for 2 h and then used in the recycling study. The experiments were conducted in a similar way and analyzed as that described in example 9. Cyclohexene conversion=92%, cvcichexene epoxide selectivity=100%.

EXAMPLE 18

This example illustrate the application of Ti—SBA-16 (Si/Ti=20, example 5) as a Lewis acid catalyst for ring opening of epoxides with amine. 50 mg of Ti—SBA-16, 20 mmol of styrene oxide and 20 mmol of aniline were taken in a double-necked round-bottom flask (50 ml) placed in a temperature-controlled oil bath and fitted with a water-cooled condenser. The reaction was conducted at 308 K and for 6 h. Then, an aliquot of the sample was withdrawn and diluted by four times with dichloromethane. It was centrifuged and the catalyst was separated. The liquid was subjected to gas chromatographic analysis (Varian 3400; CP-SIL8CB column; 30 m-long and 0.53 mm-i.d.). The products were identified using GC-MS (Varian CP-3800; 30 m-long, 0.25 mm-i.d., and 0.25 m-thick CP-Sil8CB capillary column). They were also isolated by column chromatography (eluent: petroleum ether—ethyl acetate mixture) and characterized by $^1H$ NMR studies. Two different amino alcohol isomers (A=2-phenyl-(2-phenylamino)ethanol and B=1-phenyl-(2-phenylamino)ethanol) were formed and one of it is more predominant.

EXAMPLE 19

This example illustrated the application of Ti—SBA-16 (Si/Ti=20, example 5) as a Lewis acid catalyst for aminolysis of cyclohexen oxide with aniline. 50 mg of Ti—SBA-16, 20 mmol of cyclohexene oxide and 20 mmol of aniline were taken in a double-necked round-bottom flask (50 ml) placed in a temperature-controlled oil bath and fitted with a water-cooled condenser. The reaction was conducted at 308 K and for 6 h. Then, an aliquot of the sample was withdrawn and diluted by four times with dichloromethane. It was centrifuged and the catalyst was separated. The liquid was subjected to gas chromatographic analysis (Varian 3400; CP-SIL8CB column; 30 m-long and 0.53 mm-i.d.). The products were identified using GC-MS (Varian CP-3800; 30 m-long, 0.25 mm-i.d., and 0.25 μm-thick CP-Sil8CB capillary column). They were also isolated by column chromatography (eluent: petroleum ether—ethyl acetate mixture) and characterized by $^1H$ NMR studies. Two different amino alcohol isomers (A=trans-2-(phenylamino)cyclohexanol and B=cis-2-(phenylamino)cyclohexanol) were formed and one of it is more predominant.

EXAMPLE 20

This example illustrated the application of Ti—SBA-16 (Si/Ti=20, example 5) as a Lewis acid catalyst for ring opening of styrene oxide with o-toluidine. 50 mg of Ti—SBA-16, 20 mmol of styrene oxide and 20 mmol of o-toluidine were taken in a double-necked round-bottom flask (50 ml) placed in a temperature-controlled oil bath and fitted with a water-cooled condenser. The reaction was conducted at 308 K and for 6 h. The products were isolated by column chromatography (eluent: petroleum ether—ethyl acetate mixture). Two different amino alcohol isomers (A=2-phenyl-(2-para-tolylamino)ethanol and B=1-phenyl-(2-para-tolylamino)ethanol) were formed and one of it is more predominant.

EXAMPLE 21

This example illustrated the application of Ti—SBA-16 (Si/Ti=20, example 5) as a catalyst for ring opening of styrene oxide with morpholine. 50 mg of Ti—SBA-16, 20 mmol of styrene oxide and 20 mmol of morpholine were taken in a double-necked round-bottom flask (50 ml) placed in a temperature-controlled oil bath and fitted with a water-cooled condenser. The reaction was conducted at 308 K and for 6 h. The products were isolated by column chromatography (eluent: petroleum ether —ethyl acetate mixture). Two different amino alcohol isomers (A=2-phenylpropane-1-ol compound with morpholine and B=1-phenylpropane-1-ol compound with morpholine) were formed and one of it is more predominant.

EXAMPLE 22

This example illustrated the application of Ti—SBA-16 (Si/Ti=30, example 4) as a catalyst for ring opening of styrene oxide with aniline. 50 mg of Ti—SBA-16, 20 mmol of styrene oxide and 20 mmol of aniline were taken in a double-necked round-bottom flask (50 ml) placed in a temperature-controlled oil bath and fitted with a water-cooled condenser. The reaction was conducted at 308 K and for 6 h. The products were isolated by column chromatography (eluent: petroleum ether—ethyl acetate mixture). Two different amino alcohol isomers (A=2-phenyl-(2-phenylamino)ethanol and B=1-phenyl-(2-phenylamino)ethanol) were formed and one of it is more predominant.

The Results of Examples 18-22 are Listed in Table 2

TABLE 2

| | Ti-SBA-16 (Si/Ti = 20, 2 M) | | |
|---|---|---|---|
| Example No. | Epoxide conversion (%) | Product (%) A | selectivity B |
| 18 | 96.1 | 93.0 | 7.0 |
| 19 | 72.3 | 100 | 0 |
| 20 | 88.2 | 93.2 | 6.8 |
| 21 | 67.8 | 99.4 | 0.6 |
| 22 | 33.5 | 99.2 | 0.8 |

Many modifications, substitutions and variations of the present invention are possible and apparent to those skilled in the art. The present invention can be practiced other than specifically described in the examples and should be limited in scope and breadth only by the appended claims.

Advantages of instant invention are as following:
1. Process that produces titanosilicates with Ti in tetrahedral framework locations
2. Highly efficient and selective heterogeneous, solid titanosilicate catalyst
3. Reusable catalyst and process
4. 100% epoxides selectivity in oxidations of bulkier cyclic olefins

We claim:

1. A process for the preparation of ordered mesoporous titanosilicate (Ti—SBA-16) wherein the composition of mesoporous titanosilicate has a three dimensional cubic interconnected pore structure and is represented by the formula $$Ti_xSi_{1-x}O_2$$

wherein x ranges from 0.001-0.05, with Ti is in a tetrahedral geometry and exclusively substituted for Si in the silica framework, wherein said process comprising the steps of:
 a. reacting F127 tri-block co-polymer ($EO_{106}$-$PO_{70}$-$EO_{106}$; average mol. wt. 12,600) dissolved in water and conc. HCl with tetraethyl orthosilicate and titanium isopropoxide dissolved in isopropanol at 298-313 K for a period ranging about 2hrs.
 b. stirring the reaction mixture as obtained in step (a) for 20-24 hours to form a gel;
 c. crystallising the gel as obtained in step (b) at 353-373 K for 40-50 h to obtain titanosilicate (Ti—SBA-16);
 d. washing titanosilicate as obtained in step (c) with water and drying at 373-423 K followed by calcining in air at 823 K for 6-12 h to obtain titanosilicate (Ti—SBA-16).

2. The process as claimed in claim 1, wherein mole ratio of the F127 triblock copolymer ranges between 0.55-0.6 moles.

3. An improved process for oxidation of aromatics selected from the group consisting of cyclohexene, cyclooctene, cyclohexanone, and naphthalene using titanosilicate catalyst, wherein the said process comprises the steps of:
 a charging an ordered mesoporous titanosilicat (Ti—SBA-16) wherein the composition of mesoporous titanosilicate has a three dimensional structure and is represented by the formula $$Ti_xSi_{1-x}O_2,$$

wherein x ranges from 0.001-0.05, with Ti is in a tetrahedral geometry and exclusively substituted for Si in the silica framework aromatic reactant and a oxidant in molar ratio in the range of 0.5 to 2 with respect to aromatic reactant, a solvent and optionally ammonia in a flask;
 b heating the reaction mixture as obtained in step (a) at 313-353 K for 6 to 24hrs to obtain desired product.

4. The process as claimed in claim 3, wherein solvent used in step (a) is selected from the group of dichloromethane, chloroform, dichloroethane, acetone, water and acetonitrile.

5. The process as claimed in claim 3, wherein the oxidant used in step (a) is selected from the group of non-aq. TBHP (tert. Butyl hydroperoxide), $H_2O_2$, cumene hydroperoxide and 70% aq TBHP.

6. The process as claimed in claim 3, wherein said titanosilicate is used as catalyst in the range of 3-13% with respect to aromatic reactant.

7. The process as claimed in claim 3, wherein said titanosilicate is reusable.

8. The process as claimed in claim 3, wherein conversion of the aromatic reactant ranges between 80 to 92.7% and selectivity of product ranges between 93-100%.

9. The process of claim 1, wherein the molar ratio of Si/Ti in the titanosilicate ranges from 20-120.

* * * * *